US008702674B2

(12) United States Patent
Bochenko

(10) Patent No.: US 8,702,674 B2
(45) Date of Patent: Apr. 22, 2014

(54) MEDICATION AND IDENTIFICATION INFORMATION TRANSFER APPARATUS

(75) Inventor: Walter John Bochenko, Encinitas, CA (US)

(73) Assignee: CRISI Medical Systems, Inc., Rancho Santa Fe, CA (US)

( * ) Notice: Subject to any disclaimer, the term of this patent is extended or adjusted under 35 U.S.C. 154(b) by 161 days.

(21) Appl. No.: 12/768,509

(22) Filed: Apr. 27, 2010

(65) Prior Publication Data

US 2011/0264069 A1 Oct. 27, 2011

(51) Int. Cl.
*A61B 19/00* (2006.01)

(52) U.S. Cl.
USPC .......... 604/404

(58) Field of Classification Search
USPC .......... 604/404
See application file for complete search history.

(56) References Cited

U.S. PATENT DOCUMENTS 4,650,475 A * 3/1987 Smith et al. .......... 604/189
4,853,521 A 8/1989 Claeys et al.
4,978,335 A 12/1990 Arthur, III
5,011,032 A 4/1991 Rollman
5,078,683 A 1/1992 Sancoff et al.
5,279,576 A * 1/1994 Loo et al. .......... 604/187
5,383,858 A 1/1995 Reilly et al.
5,628,309 A 5/1997 Brown
5,651,775 A 7/1997 Walker et al.
5,692,640 A * 12/1997 Caulfield et al. .......... 221/70
5,782,814 A 7/1998 Brown et al.
5,792,117 A 8/1998 Brown
5,873,731 A 2/1999 Prendergast
5,984,901 A * 11/1999 Sudo et al. .......... 604/227
6,019,745 A 2/2000 Gray
6,123,686 A 9/2000 Olsen et al.
6,192,945 B1 2/2001 Ford et al.
6,338,200 B1 1/2002 Baxa et al.
6,468,424 B1 10/2002 Donig et al.
6,579,231 B1 6/2003 Phipps
RE38,189 E 7/2003 Walker et al.
6,626,862 B1 9/2003 Duchon et al.
D481,121 S 10/2003 Evans
D485,356 S 1/2004 Evans (Continued)

FOREIGN PATENT DOCUMENTS

DE 29617777 U1 12/1996

OTHER PUBLICATIONS

International Search Report dated Aug. 2, 2011 for corresponding PCT Application No. PCT/US2010/055322.

*Primary Examiner* — Susan Su
*Assistant Examiner* — Guy K Townsend
(74) *Attorney, Agent, or Firm* — Mintz Levin Cohn Ferris Glovsky and Popeo, P.C.

(57) ABSTRACT

A medication and identification information transfer system is provided that includes a medication vial, a secondary medication container (syringe) and a medication information transfer apparatus. The medication information transfer apparatus, when coupled to a vial, can transfer information indicative of the contents of the vial to an intelligent injection site. The medication information transfer apparatus has a shape and size enabling it to be connected to a vial adapter for removal of medication from the vial transfer it to a syringe for delivery to an injection site while simultaneously transferring information about the medication in the vial to the injection site. In some implementations, the medication injection site can be placed on a fluid delivery line for infusion into a patient. Related apparatus, systems, and kits are also disclosed.

18 Claims, 8 Drawing Sheets

(56) References Cited

U.S. PATENT DOCUMENTS 6,685,678 B2 * 2/2004 Evans et al. .................. 604/207
6,790,198 B1 9/2004 White et al.
6,960,192 B1 11/2005 Flaherty et al.
7,017,623 B2 3/2006 Tribble et al.
7,074,209 B2 7/2006 Evans et al.
7,115,113 B2 * 10/2006 Evans et al. .................. 604/189
7,117,041 B2 10/2006 Engleson et al.
7,161,488 B2 * 1/2007 Frasch ...................... 340/572.1
7,236,936 B2 6/2007 White et al.
7,470,266 B2 12/2008 Massengale et al.
7,722,083 B2 * 5/2010 McCarthy et al. .............. 283/81
7,727,196 B2 6/2010 Neer
7,813,939 B2 10/2010 Clements et al.
7,834,816 B2 11/2010 Marino et al.
7,976,508 B2 7/2011 Hoag
7,991,627 B2 8/2011 Hutchinson et al.
8,035,517 B2 * 10/2011 Gibson ...................... 340/572.1
8,133,178 B2 3/2012 Brauker et al.
8,151,835 B2 4/2012 Khan et al.
8,328,082 B1 12/2012 Bochenko et al.
2001/0056258 A1 * 12/2001 Evans .......................... 604/131
2002/0040208 A1 4/2002 Flaherty et al.
2002/0088131 A1 7/2002 Baxa et al.
2002/0098598 A1 7/2002 Coffen et al.
2002/0099334 A1 7/2002 Hanson et al.
2002/0177811 A1 11/2002 Reilly et al.
2002/0188259 A1 * 12/2002 Hickle et al. .................. 604/189
2003/0012701 A1 1/2003 Sangha et al.
2003/0052787 A1 3/2003 Zerhusen et al.
2003/0055685 A1 3/2003 Cobb et al.
2003/0065537 A1 4/2003 Evans
2003/0088238 A1 5/2003 Poulsen et al.
2003/0139701 A1 7/2003 White et al.
2003/0139706 A1 7/2003 Gray
2003/0140929 A1 7/2003 Wilkes et al.
2003/0174326 A1 9/2003 Rzasa et al.
2004/0051368 A1 3/2004 Caputo et al.
2004/0082918 A1 4/2004 Evans et al.
2004/0092885 A1 5/2004 Duchon et al.
2004/0103951 A1 * 6/2004 Osborne et al. ................. 141/27
2004/0104271 A1 6/2004 Martucci et al.
2004/0186437 A1 9/2004 Frenette et al.
2004/0204673 A1 10/2004 Flaherty
2005/0055242 A1 3/2005 Bello et al.
2005/0101905 A1 5/2005 Merry
2005/0106225 A1 5/2005 Massengale et al.
2005/0107923 A1 5/2005 Vanderveen
2005/0165559 A1 7/2005 Nelson
2005/0182358 A1 8/2005 Veit et al.
2005/0277890 A1 12/2005 Stewart et al.
2006/0079767 A1 4/2006 Gibbs et al.
2006/0079843 A1 4/2006 Brooks et al.
2006/0116639 A1 6/2006 Russell
2006/0122577 A1 6/2006 Poulsen et al.
2006/0144942 A1 7/2006 Evans et al.
2006/0226089 A1 10/2006 Robinson et al.
2006/0229551 A1 10/2006 Martinez et al.
2006/0253346 A1 11/2006 Gomez
2006/0258985 A1 11/2006 Russell
2006/0265186 A1 11/2006 Holland et al.
2007/0043335 A1 2/2007 Olsen et al.
2007/0135765 A1 6/2007 Miller et al.
2007/0136218 A1 6/2007 Bauer et al.
2007/0166198 A1 7/2007 Sangha et al.
2007/0167919 A1 7/2007 Nemoto et al.
2007/0191787 A1 8/2007 Lim et al.
2007/0279625 A1 12/2007 Rzasa et al.
2007/0299421 A1 * 12/2007 Gibson ......................... 604/506
2008/0045930 A1 2/2008 Makin et al.
2008/0051937 A1 2/2008 Khan et al.
2008/0061153 A1 3/2008 Hickle et al.
2008/0125724 A1 5/2008 Monroe
2008/0191013 A1 8/2008 Liberatore
2008/0208042 A1 8/2008 Ortenzi et al.
2008/0234630 A1 9/2008 Iddan et al.
2008/0243088 A1 10/2008 Evans
2008/0294108 A1 11/2008 Briones et al.
2009/0018494 A1 1/2009 Nemoto et al.
2009/0030730 A1 1/2009 Dullemen et al.
2009/0036846 A1 2/2009 Dacquay et al.
2009/0043253 A1 2/2009 Podaima
2009/0069714 A1 3/2009 Eichmann et al.
2009/0085768 A1 4/2009 Patel et al.
2009/0149744 A1 6/2009 Nemoto et al.
2009/0157008 A1 6/2009 Vitral
2009/0159654 A1 6/2009 Grimard
2009/0294521 A1 12/2009 de la Huerga
2010/0065643 A1 3/2010 Leyvraz et al.
2010/0152562 A1 6/2010 Goodnow et al.
2010/0153136 A1 6/2010 Whittacre et al.
2010/0174266 A1 7/2010 Estes
2010/0262002 A1 10/2010 Martz
2010/0280486 A1 11/2010 Khair et al.
2010/0305499 A1 12/2010 Matsiev et al.
2011/0060198 A1 3/2011 Bennett et al.
2011/0093279 A1 4/2011 Levine et al.
2011/0111794 A1 * 5/2011 Bochenko et al. ......... 455/556.1
2011/0112473 A1 * 5/2011 Bochenko et al. .............. 604/68
2011/0112474 A1 * 5/2011 Bochenko et al. .............. 604/68
2011/0152824 A1 6/2011 DiPerna et al.
2011/0160655 A1 6/2011 Hanson et al.
2011/0176490 A1 7/2011 Mehta et al.
2011/0220713 A1 9/2011 Cloninger
2011/0224649 A1 9/2011 Duane et al.
2011/0264069 A1 * 10/2011 Bochenko ..................... 604/404
2012/0037266 A1 2/2012 Bochenko
2012/0041355 A1 2/2012 Edman et al.
2012/0323208 A1 12/2012 Bochenko et al.
2012/0325330 A1 12/2012 Prince et al.
2013/0018356 A1 1/2013 Prince et al.
2013/0135388 A1 5/2013 Samoto et al.
2013/0204227 A1 8/2013 Bochenko et al.
2013/0225945 A1 8/2013 Prince et al.

* cited by examiner

MEDICATION AND IDENTIFICATION INFORMATION TRANSFER APPARATUS

FIELD

The subject matter described herein relates to a medication and identification information transfer apparatus for use with identifying the contents of medication containers such as syringes, vials, and medication bags.

BACKGROUND

Many health care procedures involve a sequence of medication administrations to complete a specialized protocol. The type of medication and timing of administration are important to record in order to provide healthcare providers real-time information on the conduct of the procedure and the completion of a medical record. Some specialized protocols require quick medication administrations with limited time for documentation and record keeping. Pharmaceutical manufacturers produce many types of medication containers and include prefilled syringes, vials and bags.

SUMMARY

In one aspect, a medication and information transfer apparatus is provided that includes an information transfer element, an information element affixed to, deposited to, or forming an integral part of the transfer element and a vial adapter. The information transfer element includes a fluid inlet fitting and a fluid outlet fitting. The information element can fluidically couple to a vial adapter at the fluid outlet. The information element can fluidically couple to a secondary container (an empty syringe) at the fluid inlet. The information element is disposed on the information transfer element and contains information indicative of the contents of a primary medication container (vial).

The shape and size of the information transfer element is such that it can mate with the housing of a medication injection site (that in turn can determine the contents of the medication vial/container using the information transfer element). The shape and size of the vial adapter spike and vial clips can be such that it provides access to large and small medication vials. However, in some implementations, the size of the vial adapter female luer fitting is only one size.

The information transfer element fluid inlet is a female luer fitting having a surface that engages the male luer fitting tip of a syringe and will retain the information transfer element when the syringe is removed from the vial adapter. The empty syringe is used to withdraw medication from a vial containing medication for transfer to an injection site. The information transfer element fluid outlet is a male luer fitting having a surface that can disengage from the female luer fitting of the vial adapter.

The syringe can be a suitable size that is equal to or greater than the volume of medication to be withdrawn from the vial. The vial can contain a single dose volume of medication or a multiple dose volume of medication. The information on the information transfer element can contain the appropriate single dose volume.

A removable sterility cap can be affixed to the information transfer element fluid inlet for the protection of sterility. The spike of the vial adapter can contain a removable sterility cap for protection of sterility. When used these sterility caps are removed. Alternatively, the information transfer element fluid inlet can be a needleless access port allowing multiple syringes to be used for multiple withdrawals from a multi-dose vial. Alternatively, the vial adapter female luer fitting can be a needleless access port allowing multiple connections of the information transfer element to be used for multiple withdrawals from a multi-dose vial.

The medication information transfer apparatus can be enveloped in a sterile pouch (i.e., enclosure, etc.). The sterile pouch can contain information indicative of the information on the information transfer element. The medication information transfer apparatus can be part of a kit that also contains the vial and medication instructions for use. The kit can be manufactured complete by a pharmaceutical company including the medication in the vial and the information transfer apparatus. The kit can be packaged by a local pharmacy and can include a pharmaceutical company packaged vial and the information transfer apparatus. In the pharmacy kit configuration the pharmacy can match and verify the medication information on the vial and vial packaging with the medication information on the information transfer apparatus packaging and the information transfer element. Once matched and verified the pharmacy can join the vial and information transfer apparatus into a secondary package and label the kit. The secondary package can provide a tamper evident element providing assurance of maintaining the matched elements.

The identification member can be disposed radially about a central fluid outlet axis of the fluid outlet tip enabling detection of the information when the medication container is rotated about the central fluid outlet axis. The identification member can be a ring shaped member configured to fit around the fluid outlet tip of the information transfer element.

The information can be selected from a group comprising: optically encoded information, magnetically encoded information, radio frequency detectable information, capacitively and/or inductively detectable information and mechanically detectable information.

In one aspect, a system can include a medication vial, a secondary medication container, and an information transfer apparatus. The medication vial contains medication. The secondary medication container receives or extracts the medication contained within the medication vial when the secondary medication container is in fluid communication with the medication vial. The information transfer apparatus is configured to couple to the medication vial and to the secondary medication container such that, subsequent to the secondary medication container being in fluid communication with the medication vial, at least a portion of the information transfer apparatus physically transfers from the medication vial to the secondary medication container. In addition, the information transfer apparatus includes an information element to enable characterization of the medication.

In another aspect, a system includes a medication vial, a secondary medication container, and an information transfer apparatus. Unlike implementations in which the information transfer apparatus is first coupled to the medication vial, in this arrangement, the information transfer remains coupled to the secondary medication container. With such variations, the information transfer apparatus can include an information transfer element, a vial adapter configured to couple to the information transfer element on a first end and to pierce and to couple to the medication vial on a second end, and an information element characterizing medicine contained with the medication vial.

Various combinations of the medication vial, the secondary medication container, and the information transfer apparatus can be packaged together to form a portion of a kit. The packaging can be shrink wrap or other plastic enclosure or it can be a cardboard box. Additionally within or on the packaging instructions can be provided to ensure that one or more of the medication vial, the secondary medication container, and the information transfer apparatus include the correct or matching identifiers.

The details of one or more variations of the subject matter described herein are set forth in the accompanying drawings and the description below. Other features and advantages of the subject matter described herein will be apparent from the description and drawings, and from the claims.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed embodiments. In the drawings.

Like reference symbols in the various drawings indicate like or similar elements.

DETAILED DESCRIPTION

Figure 1:
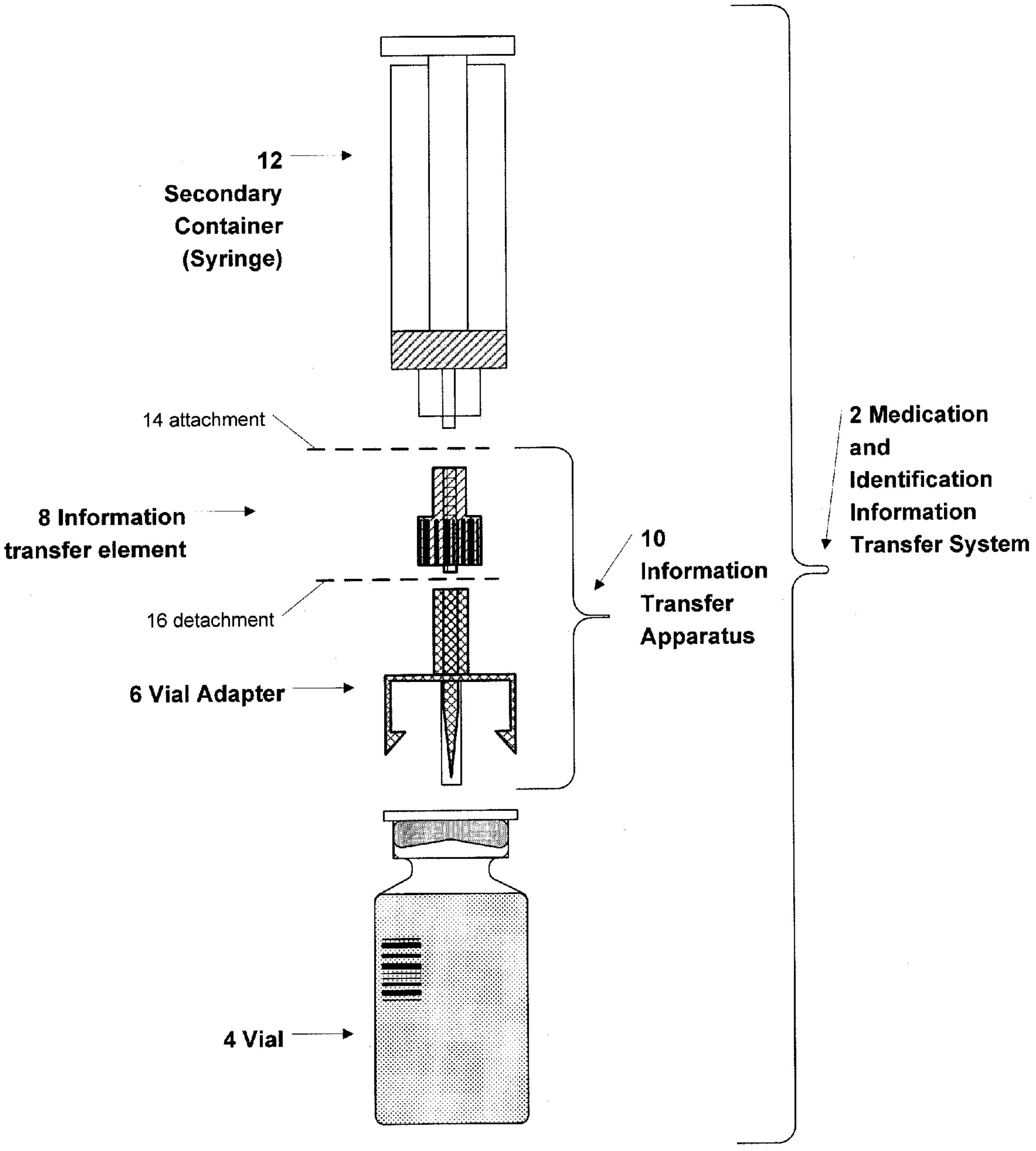
FIG. 1 is a diagram illustrating a medication and identification information transfer system.

FIG. 1 is a diagram illustrating a medication and identification information transfer system 2 in which a healthcare provider can access medication from vial 4 for transfer and administration to a patient. In particular, the healthcare provider can select vial 4 from an array of available vials and transfer the medication and medication information to a patient's medication injection site. Examples of medication injection sites and related data collection systems are described in U.S. patent application Ser. Nos. 12/614,276 and 12/765,707 both entitled "Medication Injection Site and Data Collection System", the contents of both are hereby fully incorporated by reference.

Vial adapter 6 and information transfer element 8 can be joined to form information transfer apparatus 10. Information transfer apparatus 10 can be used to puncture vial 4 to access the medication for transfer to secondary container 12 (a syringe). Syringe 12 can initially be provided empty and can be attached 14 to information transfer apparatus 10 for the purpose of withdrawing medication from vial 4. The healthcare provider withdraws medication from vial 4 into syringe 12 and detaches 16 syringe 12 from vial 4 carrying with it information transfer element 8. Syringe 12 and the medication contents are now identified for transfer to a patient for injection. A health care provider can inject the medication in syringe 4 by first attaching or otherwise coupling information transfer element 8 to an intelligent medication injection site (not shown), at time of attachment to the injection site medication information contained on information transfer element 8 (described later) can be identified by the injection site (or other device) so that the medication injected into the patient can be identified and/or logged.

Figure 2:
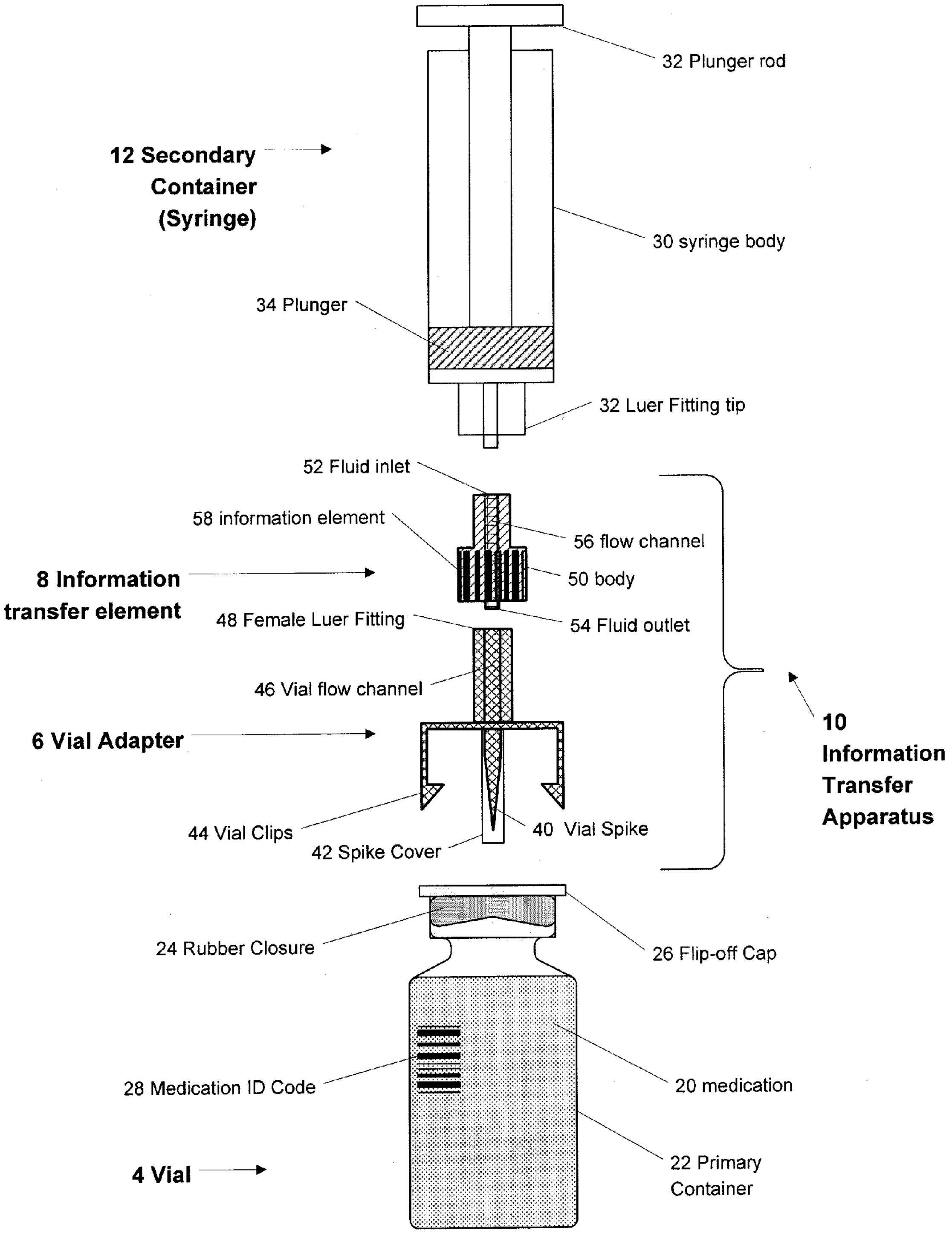
FIG. 2 is a diagram describing a detailed view of a medication and identification information transfer system as in FIG. 1.

FIG. 2 is a diagram describing a detailed view of a medication and identification information transfer system 2 as in FIG. 1. At the bottom of the figure, medication vial 4 contains medication 20 within primary container 22. At the top of vial 4 the open end of primary container 22 can be closed by rubber closure 24 and protected by flip off cap 26. Vial 4 can carry an information source 28 (e.g., medication ID code, etc.) that provides detectable information indicative of the medication in primary container 22 and/or of the volume of the contents. Vial 4 as used herein refers to both vials and other medication containers such as bags (except when explicitly disclaimed). It can be appreciated that many configurations of vial 4 can be manufactured and can function in system 2.

At the top of the figure, secondary container 12 can be a syringe with syringe body 30, luer fitting tip 32, plunger 34 and plunger rod 36. It can be appreciated that many configurations of secondary container 12 can be manufactured and can function in system 2.

In the center of FIG. 2 information transfer apparatus 10 consists of vial adapter 6 joined with information transfer element 8. Vial adapter 6 can be a sterilizable plastic material and consists of vial spike 40 with spike cover 42, vial clips 44, vial flow channel 46 and a female luer fitting 48. It can be appreciated that many configurations of vial adapter 6 can be manufactured and can function in system 2 (provided that the vial adapter can create a sterile fluid pathway between the vial and the secondary medication container).

A key aspect of the current subject matter is information transfer element 8 which can be a sterilizable injection molded plastic material consisting of element body 50, fluid inlet 52, fluid outlet 54, flow channel 56 and information element 58.

Information element 58 can be one or more of an optical source, a magnetic source, a mechanical source, a switchable RFID source, a conductive source, and/or a proximity source. One implementation can provide information encoded within information element 58 in the form of an optically detectable surface, reflective or absorbing light, that is embedded into or on top of element body 50.

Alternatively, information provided by information element 58 can be a magnetically detectable strip similar to a credit card magnetic strip, facilitating a magnetic scan similar to credit card swiping, that is embedded into or on top of element body 50.

Further and alternatively, information provided by information element 58 can be a mechanically detectable feature consisting of Braille like features of bumps or ridges or valleys on the surface of or at the end of element body 50, facilitating mechanical detection by a microswitch or similar physical detection method.

Further and alternatively, information provided by information element 58 can be an RFID tag located on the surface of element body 50, facilitating detection by an RFID reader.

The antenna of the RFID tag can be switchable and would be OPEN prior to connection to a medication injection site. Upon connection to the medication injection site the antenna can become CLOSED (or connected) facilitating RFID reader detection. When the transfer apparatus 10 is disconnected from the medication injection site the RFID tag antenna can again become OPEN.

Further and alternatively, information provided by information element 58 can be in the form of a capacitive or inductive proximity feature on the surface of or embedded into element body 50, facilitating capacitive or inductive proximity detection.

The information element 58 can be an integrated feature of the information transfer element 8 such as etched or molded features. The information element 58 can alternatively be adhered or deposited to element body 50 (i.e., information element 58 can be a label, etc.) or embedded therein. In addition, the information element 58 can be a separate element that extends around fluid outlet 54.

When information transfer apparatus 10 is manufactured, vial adapter 6 can be joined with information transfer element 8 by attaching fluid outlet 54 to female luer fitting 48. This assembly can be packaged, sterilized and provided together with vial 6 or provided separately. The packaging configurations will be described later.

Figure 3:
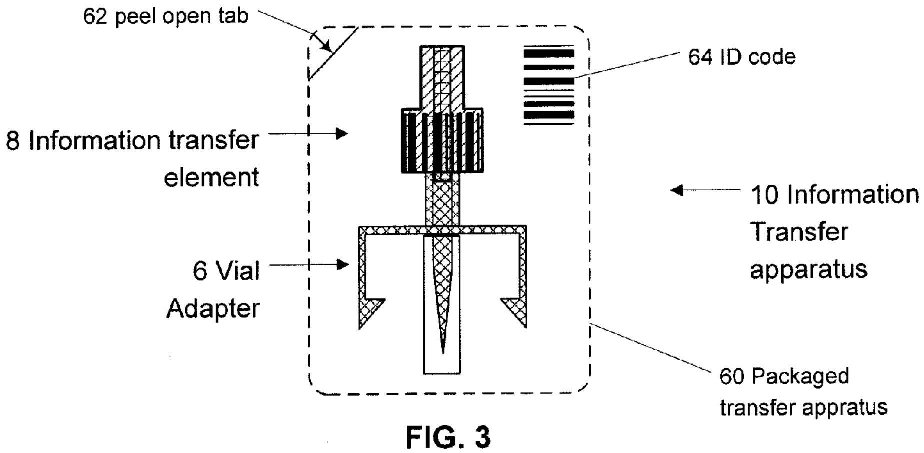
FIG. 3 is diagram illustrating a medication information transfer apparatus.

FIG. 3 is diagram illustrating medication information transfer apparatus 10 as assembled for use. The assembly can be provided in package 60 with peel open tab 62 and ID code 64. ID code 64 can be provided on the outside of package 60 and can be directly related to the information contained in information source 58 inside. ID code 64 can be used by pharmaceutical company manufacturing personnel or equipment during the packaging of vial 4, by pharmacy personnel or equipment during the kitting of vial 4 with information transfer apparatus 10, or by health care providers or equipment during the use of the medication in vial 4.

Figure 4:
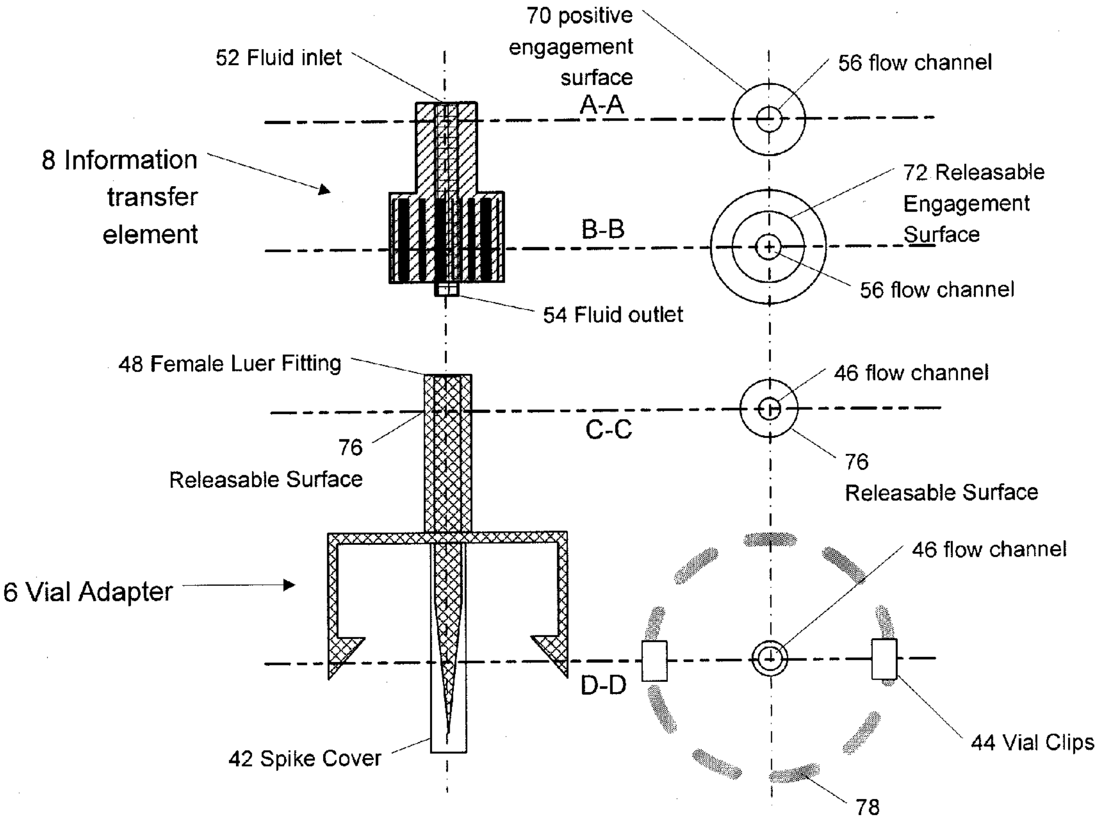
FIG. 4 is a diagram describing a detailed cross-sectional view of a medication information transfer apparatus as in FIG. 3.

FIG. 4 is a diagram describing a detailed cross-sectional view of medication information transfer apparatus 10. Sections A-A and B-B are of information transfer element 8. Section A-A shows the cross section of fluid inlet 52. Inside can be fluid flow channel 56 and outside can be positive engagement surface 70. Section B-B shows the cross section of fluid outlet 54. Inside can be fluid flow channel 56 and outside can be releasable engagement surface 72. Sections C-C and D-D are of vial adapter 6. Section C-C shows the cross section of female luer fitting 48. Inside can be flow channel 46 and outside can be releasable surface 76. Section D-D shows the cross section of the spike end of vial adapter 6. Inside can be vial flow channel 46 and outside can be vial clips 44. There can be two or more vial clips 44 located anywhere around circumference 78.

In one implementation of information transfer element 8, engagement surface 72 and releasable surface 76 are easily detachable mating surfaces so as to allow disengagement. These surfaces can be are smooth and do not promote a restrictive engagement when a user tries to disengage information transfer element 8 from vial adapter 6. Additionally, positive engagement surface 70 promotes a restrictive engagement with luer fitting 32 of syringe 12. If syringe 12 is a slip luer fitting 32 without a luer lock, the positive engagement surface 70 can be on the inner surface of the female slip luer fitting forming fluid inlet 52. If syringe 12 is a luer lock fitting, the outer surface the positive engagement surface 70 can be on the outer surface of the luer fitting forming fluid inlet 52. Information transfer element 8 can have one or both positive engagement surfaces 70. Positive engagement surface 70 can be one or more of a threaded surface, a knurled surface, a splined surface, an etched surface, a ribbed surface, etc.

Figure 5A:
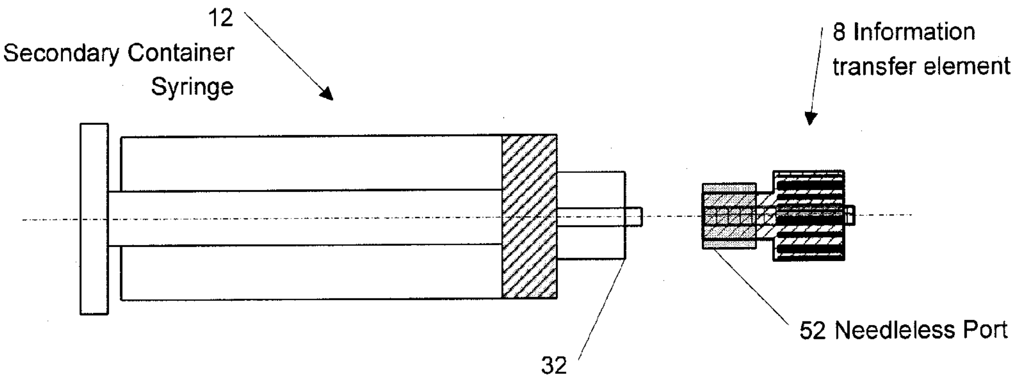
FIGS. 5A and 5B are diagrams illustrating two variations of a syringe connection to an information transfer element as in FIG. 3.
Figure 5B:
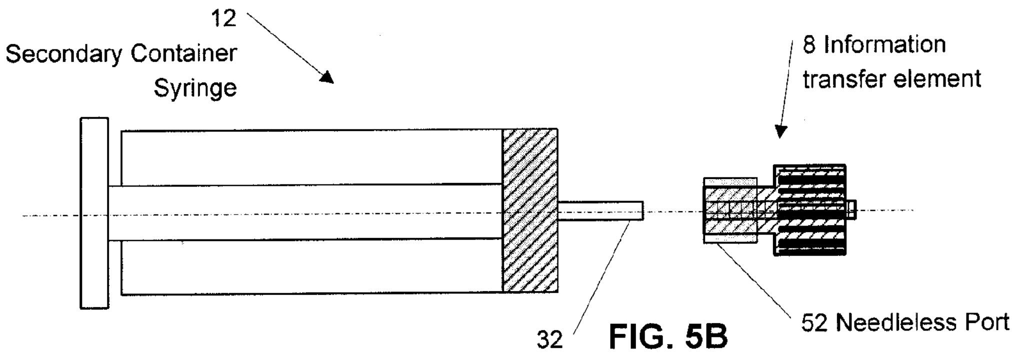
Figure 6:
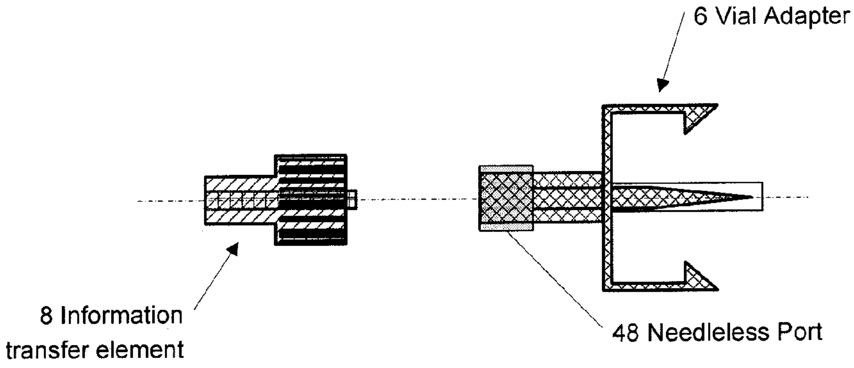
FIG. 6 depicts a variation of an information transfer element connection with a vial adapter as in FIG. 3.

There may be need for multiple medication withdrawals required from vial 4 containing a multi-dose volume of medication 20. FIGS. 5A, 5B and 6 depict the use of needleless access devices that can provide easy luer fitting and fluid access. FIGS. 5A and 5B depict information transfer element 8 with fluid inlet 52 configured as a needleless access port allowing multiple engagements of syringe 12 without the need for needles. FIG. 5A shows a luer lock type syringe tip 32 and FIG. 5B shows a luer slip type syringe tip 32. Each can access needleless access port 52 allowing multiple engagements of information transfer element 8.

FIG. 6 depicts vial adapter 6 with female luer fitting 48 configured as a needleless access port allowing multiple engagements of information transfer element 8.

Figure 7A:
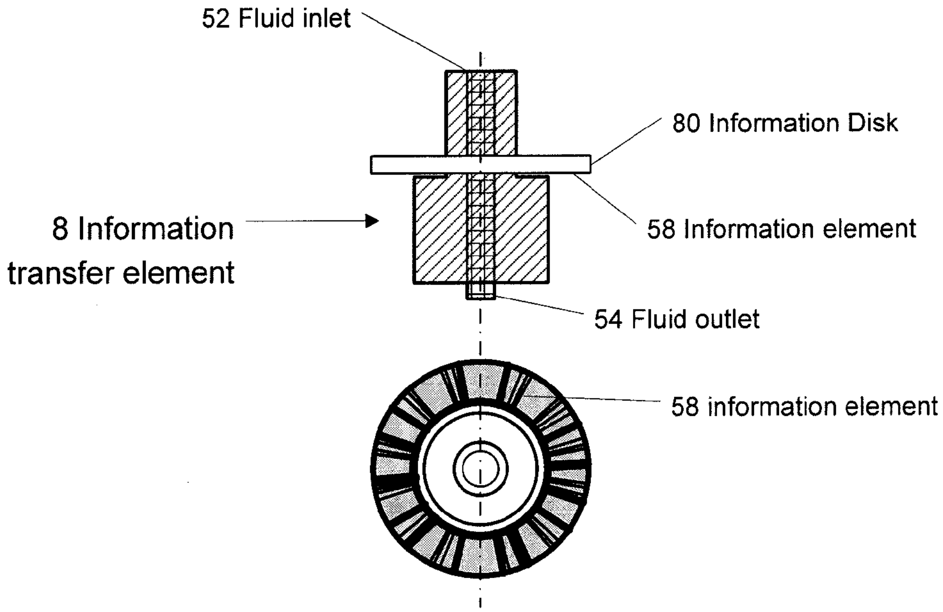
FIG. 7A is a diagram illustrating an information element as a disc.
Figure 7B:
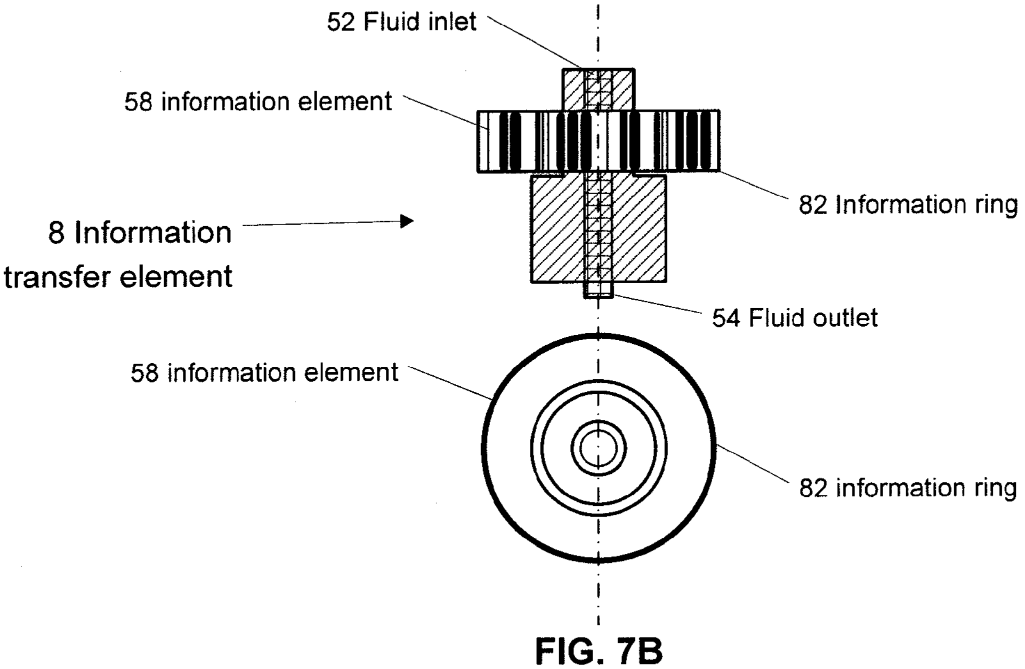
FIG. 7B is a diagram illustrating an information element as a ring.

FIGS. 7A and 7B depict an information element 58 as a disk. FIG. 7A depicts information transfer element 8 with a flat information disk 80. Information element 58 can be on a planar and annular portion of an underside of disk 80. FIG. 7B depicts information transfer element 8 with information ring 82. Information source 56 can be on a curved cylindrical outer surface of ring 82.

Figure 8:
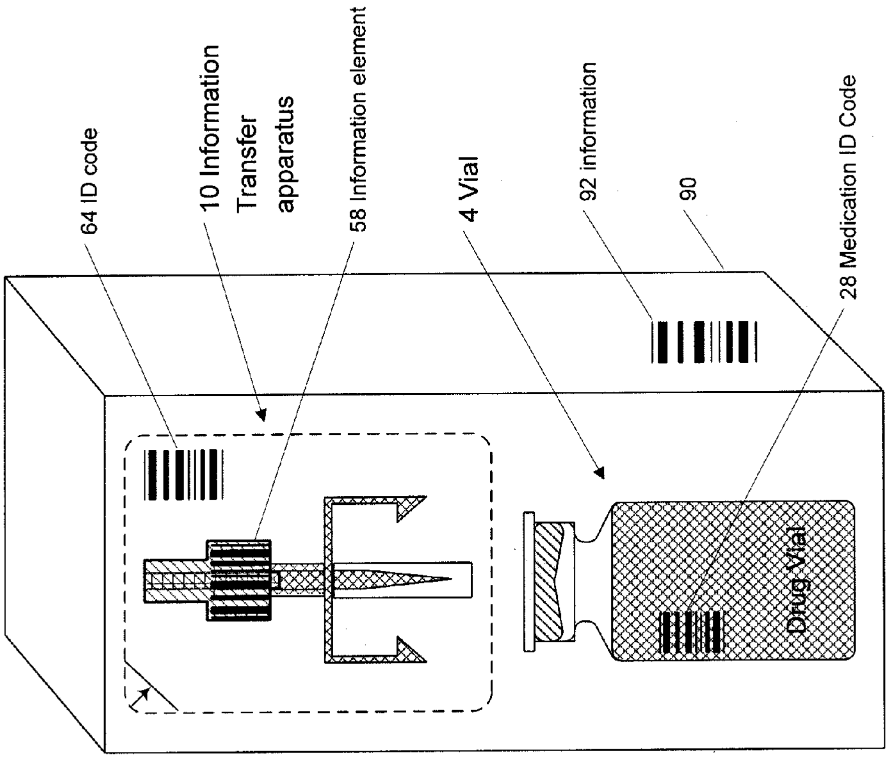
FIG. 8 is a diagram illustrating a first packaging configuration.
Figure 9:
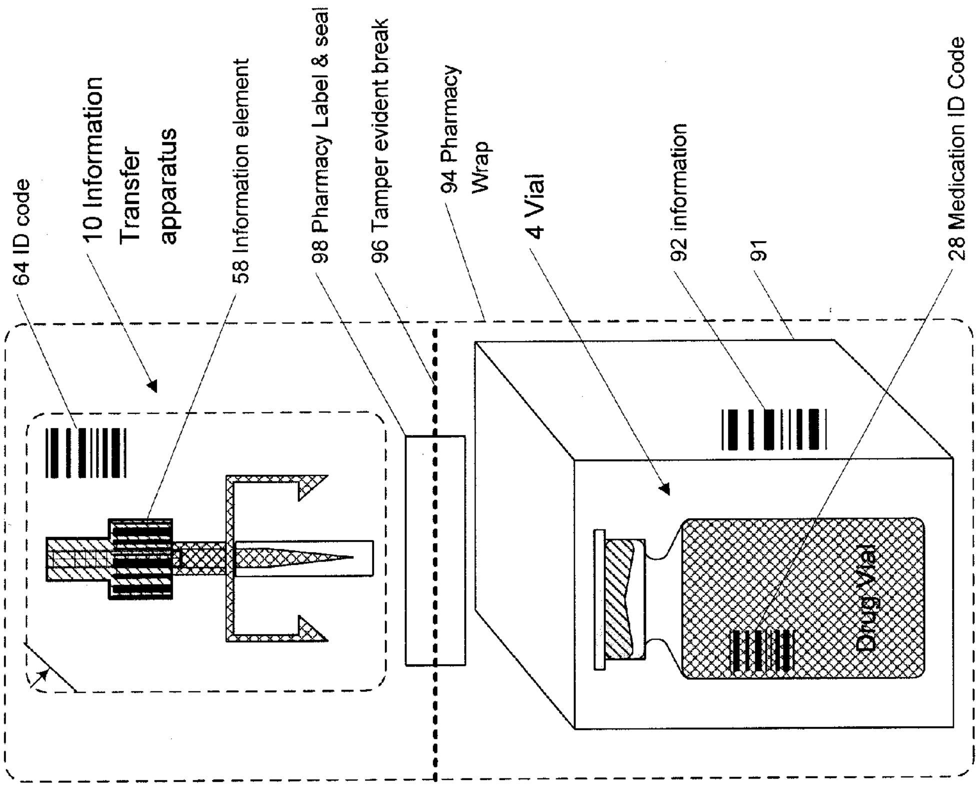
FIG. 9 is a diagram illustrating a second packaging configuration.
Figure 10:
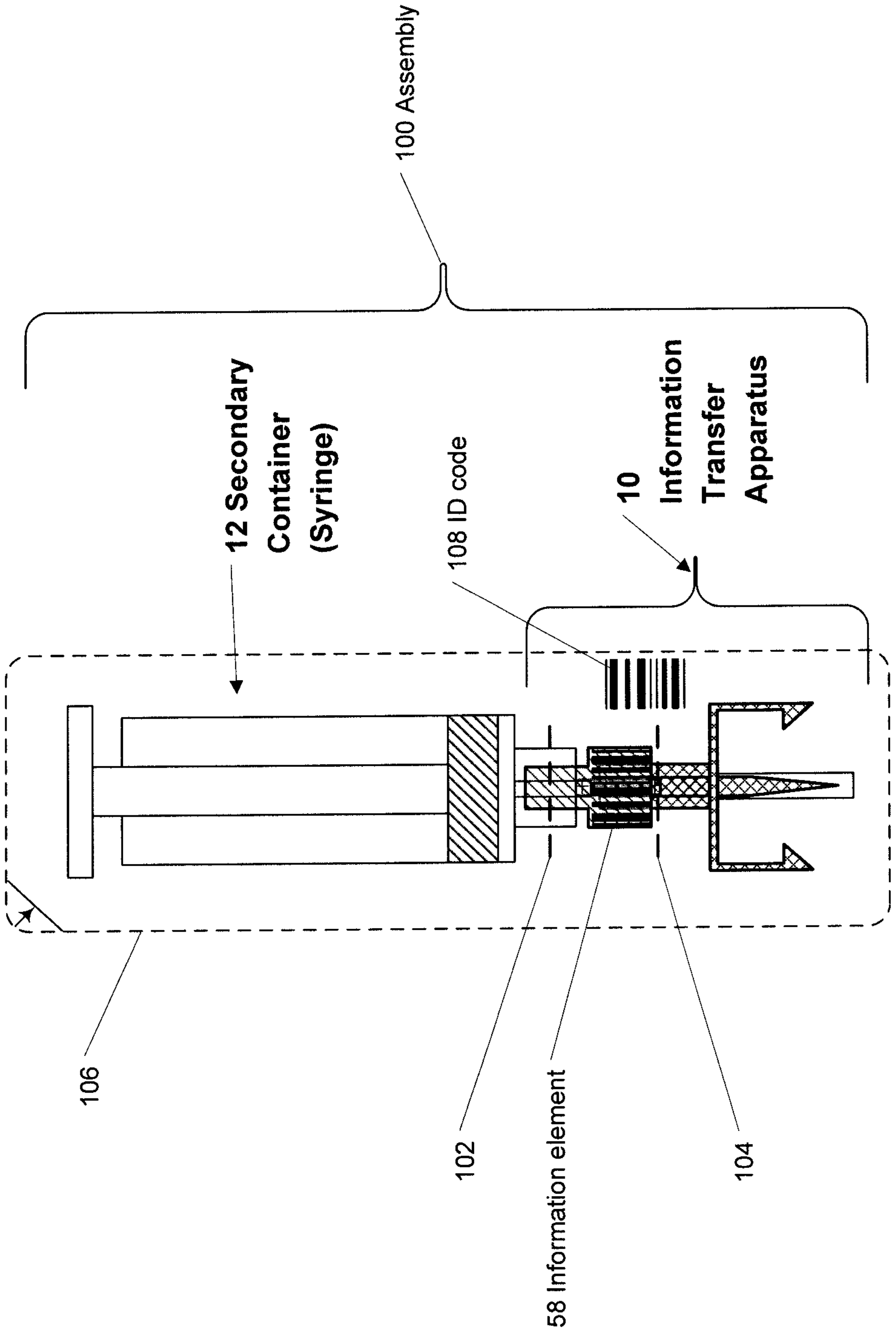
FIG. 10 is a diagram illustrating a third packaging configuration.

FIG. 8, FIG. 9 and FIG. 10 depict alternate implementations of packaging. FIG. 8 depicts a first packaging configuration that can be completed by a pharmaceutical manufacturer. In this variation, vial 4 can be packaged together with information transfer apparatus 10 in container 90. Various labeling and instructions for use (not shown) about the medication can be printed on or contained within container 90 including information 92 indicative of the contents of vial 4. Here the pharmaceutical manufacture checks and verifies that medication ID code 28, information 92, information element 58 and ID code 64 all match and are correct.

FIG. 9 depicts a second packaging configuration completed by a pharmacy. In this variation, vial 4 can be packaged in container 91 by the pharmaceutical manufacturer. Various labeling and instructions for use (not shown) about the medication can be printed on or contained within container 91 including information 92 indicative of the contents of vial 4. The pharmacy can package together vial 4 and information transfer apparatus 10 into pharmacy wrap 94. Pharmacy wrap 94 can have a tamper evident break point 96 and pharmacy seal 98 to provide assurance of package integrity. In this variation the pharmacy can check and verify that information 92 and ID code 64 match and are correct. Pharmacy label 98 can be an indication of this verification check.

FIG. 10 depicts a third packaging configuration. In this variation, a manufacturer can join secondary container 12 to transfer apparatus 10 forming assembly 100. The assembly 100 can be affixed together (bonded, snapped, latched, threaded, etc.) at point 102 such that separation is limited. In this affixed case, point 104 remains easily separable by the health care provider during use. Further, assembly 100 can be packaged in pouch 106, marked with ID code 108 and sterilized. The sterilized packaged assembly 100 can be provided to the health care provider for use. Note, that in this variation, vial 4 is provided to the health care provider separately. Similar to FIG. 9, a pharmacy can package vial 4 and assembly 100 into pharmacy wrap 94 with tamper evident break point 96 and seal 98.

Figure 11:
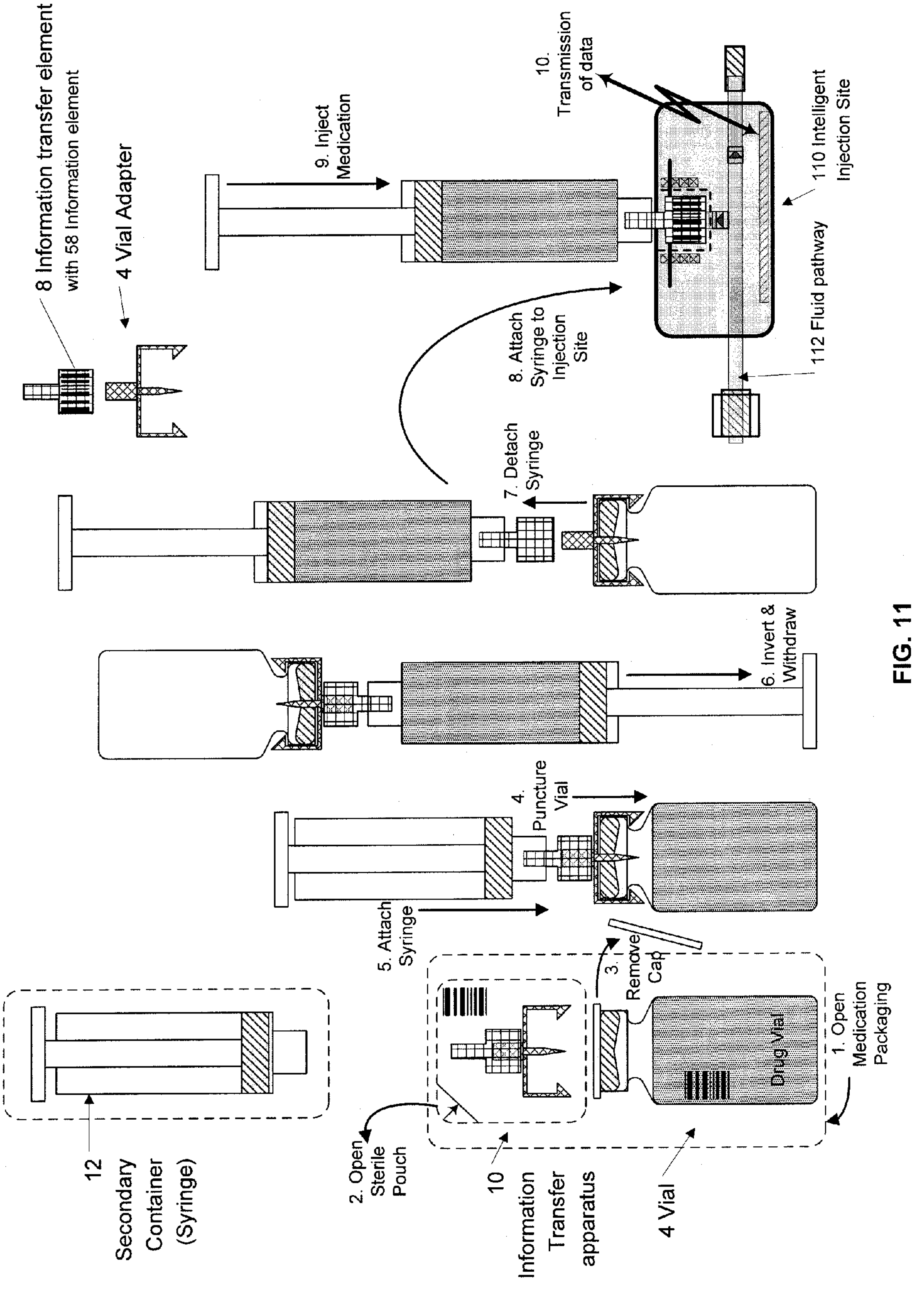
FIG. 11 is a diagram illustrating a sequence of steps describing the use of medication and identification information transfer system as in FIG. 1.

FIG. 11 is a diagram illustrating a sequence of steps describing the use of medication and identification information transfer system 2. The following steps are numbered in sequence and generally progress from left to right:

1. Open package and remove vial 4 and information transfer apparatus 10.
2. Open information transfer apparatus 10 package and remove information transfer apparatus 10.
3. Remove flip-off cap 26 from vial 4.
4. Attach information transfer apparatus 10 to vial 4 by puncturing vial 4's rubber closure 24 with spike 40.
5. Remove syringe 12 from its sterile pouch and attach to information transfer apparatus 10.
6. Invert vial 4 and information transfer apparatus 10 and withdraw medication 20 from vial 4 by pulling on plunger rod 32.
7. Detach syringe 12 with information transfer element 8 from vial adapter 6 and vial 4.
8. Attach syringe with information transfer element 8 to intelligent injection site 110.
9. Inject medication 20 into injection site 110 and fluid pathway 112.
10. Medication information is transmitted by intelligent injection site 110 to data collection system 114 (not shown). Features and functions of intelligent injection site 110, fluid pathway 112 and data collection system 114 are described in U.S. patent application Ser. Nos. 12/614,276 and 12/765,707 both entitled "Medication Injection Site and Data Collection System".

The subject matter described herein can be embodied in systems, apparatus, methods, and/or articles depending on the desired configuration. In particular, aspects of the subject matter described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications, applications, components, or code) include machine instructions for a programmable processor, and can be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows and steps for use described herein do not require the particular order shown, or sequential order, to achieve desirable results. Other embodiments can be within the scope of the following claims.

What is claimed is:

1. A system comprising:

a medication vial containing medication;

a secondary medication container to receive or extract the medication contained within the medication vial when the secondary medication container is in fluid communication with the medication vial;

an information transfer apparatus configured to fluidically couple the medication vial with the secondary medication container such that at least a portion of the information transfer apparatus physically and automatically transfers from the medication vial to the secondary medication container when the medication vial and the secondary medication container are decoupled, the information transfer apparatus having an information element to enable characterization of the medication; and a medication injection site apparatus for manually administering the medication to a patient, the medication injection site comprising a sensor positioned to automatically detect the information element on a tip of the secondary medication container when the secondary medication container is being rotated and fluidically coupled to the medication injection site apparatus.

2. A system as in claim 1, wherein the information transfer apparatus comprises:

an information transfer element; and a vial adapter configured to couple to the information transfer element on a first end and to pierce and to couple to the medication vial on a second end.

3. A system as in claim 2, wherein a fluid channel is formed through the information transfer element and the vial adapter from the medication vial on a proximal end and the secondary medication container on a distal end.

4. A system as in claim 2, wherein the information transfer element further comprises:

a connector providing a releasable connection to the vial adapter allowing a user to readily disconnect the information transfer element from the vial adapter.

5. A system as in claim 2, wherein the information transfer element further comprises:

a connector providing a non-releasable connection to the secondary medication container preventing a user from readily disconnecting the information transfer element from the secondary medication container.

6. A system as in claim 2, wherein the information transfer apparatus comprises a housing, and wherein the information transfer element is affixed to an outer surface of the housing.

7. A system as in claim 2, wherein the information transfer apparatus comprises a housing, and wherein the information transfer element is encoded or deposited on an outer surface of the housing.

8. A system as in claim 2, wherein the information transfer apparatus comprises a housing, and wherein the information transfer element is embedded within at least a portion of the housing.

9. A system as in claim 1, wherein the secondary medication container is at least a portion of a syringe.

10. A system comprising:

a medication vial containing medication;

a secondary medication container to receive or extract the medication contained within the medication vial when the secondary medication container is in fluid communication with the medication vial; and an information transfer apparatus coupled to the secondary medication container, the information transfer apparatus comprising:

an information transfer element;

a vial adapter configured to couple to the information transfer element on a first end and to pierce and to couple to the medication vial on a second end, the vial adapter comprising vial clips that couple to an outer circumference of the medication vial;

an information element characterizing medicine contained with the medication vial; and a medication injection site apparatus for manually administering the medication to a patient, the medication injection site comprising a sensor positioned to automatically detect the information element when the secondary medication container is being rotated and fluidically coupled to the medication injection site apparatus.

11. A kit comprising:

packaging enveloping:

medication vial containing medication, the medication vial having a first information source to enable characterization of the medication;

an information transfer apparatus configured to fluidically couple the medication vial with the secondary medication container such that at least a portion of the information transfer apparatus physically and automatically transfers from the medication vial to the secondary medication container when the medication vial and the secondary medication container are decoupled, the information transfer apparatus having an information element to enable characterization of the medication; and a label or document identifying the medication to ensure that the first information source matches the second information source;

wherein the information element is automatically detected a medication injection site apparatus for manually administering medication to a patient when the secondary medication container is being fluidically coupled to the medication injection site apparatus, wherein the medication injection site apparatus comprises a housing, a medication port extending from an outer surface of the housing to couple to a fluid outlet of the secondary medication container, the medication port being fluidically coupled to a patient such that medication received via the medication port is immediately administered to the patient, an identification sensor disposed within the housing to automatically generate information indicative of contents of the secondary medication container during coupling of the fluid outlet of the secondary medication container to the medication port, and a transmitter disposed within the housing and in communication with the identification sensor to wirelessly transmit the information generated by the identification sensor to a remote data collection system.

12. A kit as in claim 11, wherein the label or document are human readable.

13. A kit as in claim 11, wherein the packaging includes at least one tamper proof element, the tamper proof element when broken indicating that the packaging has been breached.

14. A kit as in claim 11, further comprising a label or document indicating that a verification that the first information source matches the second information source has been completed.

15. A kit comprising:

packaging enveloping:

a first medication container containing medication, the first medication container having a first information source to enable characterization of the medication;

an information transfer apparatus configured to couple to the first medication container and having a second information source to enable characterization of the medication, the information transfer apparatus comprising an information transfer element, and a vial adapter configured to couple to the information transfer element on a first end and to pierce and to couple to an outer circumference of the first medication container on a second end, wherein the information transfer apparatus is configured to couple the first medication container to a second medication container and to physically and automatically transfer from the first medication container to the secondary medication container when the first medication container and the secondary medication container are decoupled;

a label or document identifying the medication to ensure that the first information source matches the second information source; and wherein the information element is automatically detected a medication injection site apparatus for manually administering medication to a patient when the secondary medication container is being fluidically coupled to the medication injection site apparatus, wherein the medication injection site comprises a sensor positioned to automatically detect the information element as the secondary medication container is being rotated and fluidically coupled to the medication injection site apparatus.

16. A kit as in claim 15, wherein the label or document are human readable.

17. A kit as in claim 15, wherein the packaging includes at least one tamper proof element, the tamper proof element when broken indicating that the packaging has been breached.

18. A kit as in claim 15, further comprising a label or document indicating that a verification that the first information source matches the second information source has been completed.

* * * * *